(12) United States Patent
Cheung

(10) Patent No.: US 6,977,168 B2
(45) Date of Patent: Dec. 20, 2005

(54) METHODS AND COMPOSITIONS FOR TREATING NEPHROTIC SYNDROME

(75) Inventor: Ling Yuk Cheung, Hong Kong (HK)

(73) Assignee: Ultra Biotech Limited, Douglas (GB)

(*) Notice: Subject to any disclaimer, the term of this patent is extended or adjusted under 35 U.S.C. 154(b) by 31 days.

(21) Appl. No.: 10/717,133

(22) Filed: Nov. 18, 2003

(65) Prior Publication Data

US 2005/0106168 A1 May 19, 2005

(51) Int. Cl.$^7$ .............................. C12N 1/14; C12N 13/00
(52) U.S. Cl. ................................ 435/173.1; 435/255.1; 435/255.2; 435/173.8
(58) Field of Search .......................... 435/173.1, 255.1, 435/255.2, 173.8; 424/195.16

(56) References Cited

U.S. PATENT DOCUMENTS

| | | |
|---|---|---|
| 2,107,830 A | 2/1938 | Liebesny et al. |
| 3,150,979 A | 9/1964 | Ensley |
| 3,711,392 A | 1/1973 | Metzger |
| 3,870,599 A | 3/1975 | Azarowicz |
| 3,923,279 A | 12/1975 | Gresley et al. |
| 3,939,279 A | 2/1976 | Kawano et al. |
| 3,968,254 A | 7/1976 | Rhodes et al. |
| 3,997,675 A | 12/1976 | Eichelburg |
| 4,041,182 A | 8/1977 | Erickson et al. |
| 4,081,367 A | 3/1978 | Hulls et al. ................. 210/610 |
| 4,118,512 A | 10/1978 | Eichelburg |
| 4,183,807 A | 1/1980 | Yoshizawa et al. ......... 210/611 |
| 4,211,645 A | 7/1980 | Zajic et al. ................. 210/611 |
| 4,348,483 A | 9/1982 | Skogerson |
| 4,559,305 A | 12/1985 | Zajic et al. ................. 435/243 |
| 4,816,158 A | 3/1989 | Shimura et al. ............ 210/610 |
| 5,047,250 A | 9/1991 | Prieels et al. |
| 5,075,008 A | 12/1991 | Chigusa et al. ............. 210/610 |
| 5,082,662 A | 1/1992 | Laurent et al. |
| 5,082,936 A | 1/1992 | Jamas et al. |
| 5,106,594 A | 4/1992 | Held et al. ................. 422/292 |
| 5,158,788 A | 10/1992 | Lavens et al. |
| 5,416,010 A | 5/1995 | Langenberg et al. ........ 435/468 |
| 5,476,787 A | 12/1995 | Yokoyama et al. ......... 435/262.5 |
| 5,504,079 A | 4/1996 | Jamas et al. |
| 5,567,314 A | 10/1996 | Chigusa et al. ............. 210/150 |
| 5,578,486 A | 11/1996 | Zhang |
| 5,665,352 A | 9/1997 | Blehaut et al. |
| 5,707,524 A | 1/1998 | Potter ........................ 210/606 |
| 5,866,116 A | 2/1999 | Yaegaki |
| 5,879,928 A | 3/1999 | Dale et al. ................. 435/264 |
| 5,952,020 A | 9/1999 | Lizak |
| 5,981,219 A | 11/1999 | Flugge et al. |
| 6,036,854 A | 3/2000 | Potter ........................ 210/177 |
| 6,045,834 A | 4/2000 | Howes et al. |
| 6,143,731 A | 11/2000 | Jamas et al. |
| 6,159,510 A | 12/2000 | Lizak |
| 6,197,295 B1 | 3/2001 | Hsia et al. |
| 6,214,337 B1 | 4/2001 | Hayen et al. |
| 6,391,617 B1 | 5/2002 | Cheung ...................... 435/254 |
| 6,391,618 B1 | 5/2002 | Cheung ...................... 435/255 |
| 6,391,619 B1 | 5/2002 | Cheung ...................... 435/255 |
| 6,416,982 B1 | 7/2002 | Zhang |
| 6,416,983 B1 | 7/2002 | Cheung |
| 6,436,695 B1 | 8/2002 | Cheung ...................... 435/254 |
| 6,440,713 B1 | 8/2002 | Cheung ...................... 435/173 |
| 6,596,272 B2 | 7/2003 | Cheung |
| 6,596,273 B2 | 7/2003 | Cheung |
| 6,649,383 B1 | 11/2003 | Cheung ................... 435/173.1 |
| 6,660,508 B1 | 12/2003 | Cheung ................... 435/173.1 |
| 6,699,496 B1 | 3/2004 | Kojima et al. |
| 6,761,886 B2 | 7/2004 | Cheung |
| 6,800,466 B2 | 10/2004 | Cheung |
| 6,828,131 B2 | 12/2004 | Zhang |
| 6,828,132 B2 | 12/2004 | Cheung |

(Continued)

FOREIGN PATENT DOCUMENTS

| | | |
|---|---|---|
| CN | 1110317 A | 10/1995 |
| CN | 1207873 | 2/1999 |
| CN | 1309175 | 8/2001 |
| EP | 0041373 | 12/1981 |
| EP | 553377 | 8/1993 |
| EP | 1375652 | 1/2004 |

(Continued)

OTHER PUBLICATIONS

U.S. Appl. No. 10/192,805, filed Nov. 29, 2004, Zhang.
U.S. Appl. No. 10/192,807, filed Nov. 29, 2004, Cheung.
Bom et al., "The Saccharomyces Boulardii Therapy of HIV–Associated Diarrhea", *Deutsche Medizinische Wochenschrift*, 118(20):765 (1993). (in German with English translation).
Dutta et al., *J. of Microwave Power*, vol. 14, No. 3, pp. 275–280 (1979).
Goodman, et al., "Magnetic Field Stress Induces Expression of HSP70", *Cell Stress & Chaperones* 3(2):79–88 (1998).
Grundler W., "Resonant Microwave Effect on Locally Fixed Yeast Microcolonies" *Z. Naturforsch* 44c:863–866 (1989).
Kim et al., "Anti–Stress and Anti–Fatigue Effects of Fermented Rice Bran", *Biosci Biotechnol Biochem.*, 65(10):2294–6 (2001).
Lin H. et al., "A Magnetic Field–Responsive Domain in the Human HSP70 Promoter", *J Cell Biochem*, 75:170–176 (1999).
Machado Caetano et al., "Immunopharmacological Effects of *Saccharomyces boulardii* in Healthy Human Volunteers", *Int'l Immunology and Immunopharmacology*, 8(3):245–259 (1986).

(Continued)

*Primary Examiner*—Bruce R. Campell
*Assistant Examiner*—Randall Winston
(74) *Attorney, Agent, or Firm*—Fish & Neave IP Group; Ropes & Gray LLP; James F. Haley, Jr.

(57) ABSTRACT

Compositions comprising a plurality of yeast cells, wherein said plurality of yeast cells are characterized by their ability to treat nephrotic syndrome (e.g., lower urinary protein and increase serum protein) in a subject as a result of having been cultured in the presence of an alternating electric field having a specific frequency and a specific field strength. Also included are methods of making and using such compositions.

12 Claims, 2 Drawing Sheets

U.S. PATENT DOCUMENTS

| | | | |
|---|---|---|---|
| 2002/0099026 A1 | 7/2002 | Goodman et al. | |
| 2002/0123127 A1 | 9/2002 | Cheung | 435/254 |
| 2002/0123129 A1 | 9/2002 | Cheung | 435/254 |
| 2002/0123130 A1 | 9/2002 | Cheung | 435/262 |
| 2003/0230126 A1 | 12/2003 | Cheung | |
| 2003/0230245 A1 | 12/2003 | Cheung | |
| 2003/0232038 A1 | 12/2003 | Cheung | |
| 2003/0232039 A1 | 12/2003 | Cheung | |
| 2003/0232059 A1 | 12/2003 | Cheung | |
| 2003/0235565 A1 | 12/2003 | Cheung | |
| 2003/0235566 A1 | 12/2003 | Cheung | |
| 2003/0235567 A1 | 12/2003 | Cheung | |
| 2003/0235568 A1 | 12/2003 | Cheung | |
| 2003/0235569 A1 | 12/2003 | Cheung | |
| 2003/0235570 A1 | 12/2003 | Cheung | |
| 2004/0001812 A1 | 1/2004 | Cheung | |
| 2004/0001813 A1 | 1/2004 | Cheung | |
| 2004/0001814 A1 | 1/2004 | Cheung | |
| 2004/0001815 A1 | 1/2004 | Cheung | 424/93.51 |
| 2004/0001857 A1 | 1/2004 | Cheung | 424/195.16 |
| 2004/0001858 A1 | 1/2004 | Cheung | 424/195.16 |
| 2004/0001859 A1 | 1/2004 | Cheung | 424/195.16 |
| 2004/0001860 A1 | 1/2004 | Cheung | 424/195.16 |
| 2004/0001861 A1 | 1/2004 | Cheung | 424/195.16 |
| 2004/0005335 A1 | 1/2004 | Cheung | |
| 2004/0005337 A1 | 1/2004 | Cheung | 424/195.16 |
| 2004/0005680 A1 | 1/2004 | Cheung | |
| 2004/0168492 A1 | 9/2004 | Cheung | |
| 2004/0252492 A1 | 12/2004 | Cheung | |
| 2004/0253251 A1 | 12/2004 | Cheung | |
| 2004/0253252 A1 | 12/2004 | Cheung | |
| 2004/0253253 A1 | 12/2004 | Cheung | |
| 2004/0253254 A1 | 12/2004 | Cheung | |
| 2004/0253255 A1 | 12/2004 | Cheung | |
| 2004/0253256 A1 | 12/2004 | Cheung | |
| 2004/0253257 A1 | 12/2004 | Cheung | |
| 2004/0253258 A1 | 12/2004 | Cheung | |
| 2004/0253259 A1 | 12/2004 | Cheung | |
| 2004/0253260 A1 | 12/2004 | Cheung | |
| 2004/0253261 A1 | 12/2004 | Cheung | |
| 2004/0253262 A1 | 12/2004 | Cheung | |
| 2004/0253263 A1 | 12/2004 | Cheung | |
| 2004/0253264 A1 | 12/2004 | Cheung | |
| 2004/0253265 A1 | 12/2004 | Cheung | |
| 2004/0253266 A1 | 12/2004 | Cheung | |
| 2004/0253267 A1 | 12/2004 | Cheung | |
| 2004/0253268 A1 | 12/2004 | Cheung | |
| 2004/0265990 A1 | 12/2004 | Cheung | |

FOREIGN PATENT DOCUMENTS

| | | |
|---|---|---|
| ES | 475500 | 4/1979 |
| FR | 2222433 | 10/1974 |
| GB | 1397873 | 6/1975 |
| JP | 60028893 | 2/1985 |
| SU | 415983 A | 11/1974 |
| SU | 1071637 | 2/1984 |
| SU | 1722364 | 3/1992 |
| SU | 1750570 | 7/1992 |
| WO | WO 87/02705 | 5/1987 |
| WO | WO 95/04814 | 2/1995 |
| WO | WO 99/60142 | 11/1999 |
| WO | WO 02/20431 | 3/2002 |
| WO | WO 02/62981 | 8/2002 |
| WO | WO 02/62982 | 8/2002 |
| WO | WO 02/62983 | 8/2002 |
| WO | WO 02/62984 | 8/2002 |
| WO | WO 02/62985 | 8/2002 |
| WO | WO02070436 | 9/2002 |
| WO | WO 02/070682 A2 | 9/2002 |
| WO | WO02070683 | 9/2002 |
| WO | WO2004108919 | 12/2004 |

OTHER PUBLICATIONS

Ortuno et al., "Oral Administration of Yeast, *Saccharomyces cerevisiae*, Enhances the Cellular Innate Immune response of Gilthead Seabream (*Sparus aurata L.*)", *Vet Immunol Immunopathol*, 85(1–2):41–50 (2002).

Peret Filho et al., "Dose Effect of Oral *Saccharomyces boulardii* Treatments on Morbidity and Mortality in Immunosuppressed Mice", *J Med Microbiol.*, 47(2):111–6 (1998).

Saha et al., "Microbial Manipulation of Rumen Fermentation Using *Saccharomyces cerevisiae* as Probiotics", *Current Science (Bangalore)*, 77(5):696–697 (1999).

WHO World Health Organization; WebPages http:www.who.int/peh–emf/about/WhatisEMF/en/ and http:www.who.int/peh–emf/about/WhatisEMF/en/index3.html retrieved Jun. 10, 2004.

Agarwal N. et al., "Selection of *Saccharomyces cerevisiae* strains for use as a microbial feed additive," *Letters in Applied Microbiology*, 31:270–273 (2000).

Asami, K. et al., "Real–Time Monitoring of Yeast Cell Division by Dielectric Spectroscopy", *Biophysical Journal*, 76, pp. 3345–3348 (1999).

Balcer–Kubiczek, E.K. et al., "Expression Analysis of Human HL60 Cells Exposed to 60 Hz Square–or Sine–Wave Magnetic Fields", *Radiation Research*, 153, pp. 670–678 (2000).

Bassett, C.A.L. et al., "Beneficial Effects of Electromagnetic Fields", *Journal of Cellular Biochemistry*, 51, pp. 387–393 (1993).

Binninger, D. M. et al., "Effects of 60Hz AC magnetic fields on gene expression following exposure over multiple cell generations using *Saccharomyces cerevisiae*", *Bioelectrochemistry and Bioenergetics*, 43(1): 83–89 (1997).

Conti, P. et al., "Effect of Electromagnetic Fields on Several CD Markers and Transcription and Expression of CD4", *Immunobiology*, 201, pp. 36–48 (1999).

Deguchi, T. et al., "Nylon biodegradation by lignin–degrading fungi", *Applied and Environmental Microbiology*, 63(1): 329–331 (1997).

Dufresne C. et al., "Tea, Kombucha, and Health: A review," *Food Research International*, 33:409–421 (2000).

Gonzalez, A.M. et al., "Effects of an Electric Field of Sinusoidal Waves on the Amino Acid Biosynthesis by Azotobacter", *Z. Naturforsch*, 35, pp. 258–261 (1980).

Goodman, E.M. et al., "Effects of Electromagnetic Fields on Molecules and Cells", *International Review of Cytology*, 158, pp. 279–339 (1995).

Greenwalt C.J. et al., "Kombucha, the fermented tea: Microbiology, composition, and claimed health effects," *Journal of Food Protection*, 63:976–981 (2000).

Grospietsch, T. et al., "Stimulating Effects of Modulated 150 MHz Electromagnetic Fields on the Growth of *Escherichia coli* in a Cavity Resonator", *Bioelectrochemistry and Bioenergetics*, 37, pp. 17–23 (1995).

Grundler W. et al., "Resonant–like dependence at yeast growth rate on microwave frequencies," *The British Journal of Cancer*, Supplement, England Mar. 1982, 45:206–208 (1982).

Grundler, W. et al., "Mechanisms of Electromagnetic Interaction with Cellular Systems", *Naturwissenschaften*, 79, pp. 551–559 (1992).

Grundler, W. et al., "Nonthermal Effects of Millimeter Microwaves on Yeast Growth", *Z. Naturforsch*, 33, pp. 15–22 (1978).

Ivaschuk, O.I. et al., "Exposure of Nerve Growth Factor–Treated PC 12 Rat Pheochromocytoma Cells to a Modulated Radiofrequency Field at 836.55 MHz: Effects on c–jun and c–fos Expression", *Bioelectromagnetics*, 18, pp. 223–229 (1997).

Jelinke, F. et al., "Microelectronic Sensors for Measurement of Electromagnetic Fields of Living Cells and Experimental Results", *Bioelectrochemistry and Bioenergetics*, 48, pp. 261–266 (1999).

Lacy–Hulbert, A. et al., "Biological Responses to Electromagnetic Fields", *FASEB Journal*, 12, pp. 395–420 (1998).

Libertin, C.R. et al., "Effects of Gamma Rays, Ultraviolet Radiation, Sunlight, Microwaves and Electromagnetic Fields on Gene Expression Mediated by Human Immunodeficiency Virus Promoter", *Radiation Research*, 140, pp. 91–96 (1994).

Lin, H. et al., "Magnetic Field Activation of Protein–DNA Binding", *Journal of Cellular Biochemistry*, 70, pp. 297–303 (1998).

Lin, H. et al., "Specific Region of the c–myc Promoter Is Responsive to Electric and Magnetic Fields", *Journal of Cellular Biochemistry*, 54, pp. 281–288 (1994).

Liu C.H. et al., "The Isolation and identification of microbes from a fermented tea beverage, Haipao, and their interactions during Haipao fermentation," *Food Microbiology* (London), 13:407–415 (1996).

Loberg, L.I. et al., "Expression of Cancer–Related Genes in Human Cells Exposed to 60 Hz Magnetic Fields", *Radiation Research*, 153, pp. 679–684 (2000).

Mayser P. et al., "The yeast spectrum of the 'tea fungus Kombucha'," *Mycoses*, Blackwell, Berlin, Germany, 38:289–295 (1995).

Moore, R.L., "Biological Effects of Magnetic Fields: Studies with Microorganisms", *Canadian Journal of Microbiology*, 25, pp. 1145–1151 (1979).

Morehouse, C.A. et al., "Exposure of Daudi Cells to Low–Frequency Magnetic Fields Does Not Elevate MYC Steady–State mRNA Levels", *Radiation Research*, 153, pp. 663–669 (2000).

Norris, V. et al., "Do Bacteria Sing? Sonic Intercellular Communication Between Bacteria May Reflect Electromagnetic Intracellular Communication Involving Coherent Collective Vibrational Modes that Could Integrate Enzyme Activities and Gene Expression", *Molecular Microbiology*, 24, pp. 879–880 (1997).

Novelli, G. et al., "Study of the Effects on DNA of Electromagnetic Fields Using Clamped Homogeneous Electric Field Gel Electrophoresis", *Biomedicine & Pharmacotherapy*, 45, pp. 451–454 (1991).

Phillips, J.L., "Effects of Electromagnetic Field Exposure on Gene Transcription", *Journal of Cellular Biochemistry*, 51, pp. 381–386 (1993).

Pichko, V. B. et al., "Electromagnetic stimulation of productivity of microorganisms and its mechanisms", *Prikladnaya Biokhimiya I Mikrobiologiya*, 32(4): 468–472 (1996).

Ponne, C. T. et al., "Interaction of electromagnetic energy with biological material–relation to food processing", *Radiation Physics and Chemistry*, 45(4): 591–607 (1995).

Romano–Spica, V. et al., "Ets1 Oncogene Induction by ELF–Modulated 50 MHz Radiofrequency Electromagnetic Field", *Bioelectromagnetics*, 21, pp. 8–18 (2000).

Surawicz Christina M. et al., "The search for a better treatment for recurrent Clostridium difficile disease: Use of high–dose vancomycin combined with *Saccharomyces boulardii*," *Clinical Infectious Diseases*, 31:1012–1017 (2000).

Trosko, J.E., "Human Health Consequences of Environmentally–Modulated Gene Expression: Potential Roles of ELF–EMF Induced Epigenetic Versus Mutagenic Mechanisms of Disease", *Bioelectromagnetics*, 21, pp. 402–406 (2000).

Van den Bogaerde J. et al., "Immune sensitization to food, yeast and bacteria in Crohn's disease," *Alimentary Pharmacology & Therapeutics*, 15:1647–1653 (2001).

Van Rensburg, P. et al., "Engineering yeast for efficient cellulose degradation", *Yeast*, 14(1): 67–76 (1998).

Ventura, C. et al., "Elf–pulsed Magnetic Fields Modulate Opioid Peptide Gene Expression in Myocardial Cells", *Cardiovascular Research*, 45, pp. 1054–1064 (2000).

Woodward, A.M. et al., "Genetic Programming as an Analytical Tool for Non–linear Dielectric Spectroscopy", *Bioelectrochemistry and Bioenergetics*, 48, pp. 389–396 (1999).

Yonetani, T. et al., "Electromagnetic Properties of Hemoproteins", *The Journal of Biological Chemistry*, 247, pp. 2447–2455 (1972).

Zhang, L. et al., "Electrostimulation of the Dehydrogenase System of Yeast by Alternating Currents", *Bioelectrochemistry and Bioenergetics*, 28, pp. 341–353 (1992).

"*Saccharomyces cerevisiae* Meyen ex Hansen", China Catalogue of Cultures/China Committee of Culture Collection for Microoganisms (CCCCM), "www.im.ac.cn/database/YEAST/y122.htm", Apr. 24, 1996, retrieved on Nov. 27, 2002.

METHODS AND COMPOSITIONS FOR TREATING NEPHROTIC SYNDROME

FIELD OF THE INVENTION

The invention relates to yeast compositions that can ameliorate or prevent nephrotic syndrome and are useful as a dietary supplement (e.g., health drink) or medication. These compositions contain yeast cells obtainable by growth in electromagnetic fields with specific frequencies and field strengths.

BACKGROUND OF THE INVENTION

Nephrotic syndrome is a condition caused by a group of diseases that damage the kidney's filtering system, the glomeruli. The two main features of nephrotic syndrome are excess excretion of proteins in the urine (proteinuria) and lower level of protein in the blood (hypoalbuminemia). Other major symptoms include swelling (edema) and high level of cholesterol in the blood (hypercholesterolemia).

Nephrotic syndrome may be caused by both kidney diseases and non-kidney diseases, such as diabetes, lupus and hypertension. Primary causes include minimal change disease, focal segmental glomerulosclerosis, membranous glomerulonephritis, membranoproliferative glomerulonephritis and mesangial proliferative glomerulonephritis.

Nephrotic syndrome is usually diagnosed by clinical testing and confirmed by renal biopsy. An initial urinalysis is done to measure the amount of protein in the urine by collecting urine for 24 hours. A blood test is commonly done to detect the protein, cholesterol and triglyceride levels in the blood. It is common to have abnormal blood overclots (coagulopathies) due to the urinary loss of certain protein in patients with nephrotic syndrome. A blood test may also be used to detect serum levels of factor VIII, fibrinogen and platelets.

Treatment of nephrotic syndrome is directed at the underlying disease. Some of the diseases that cause nephrotic syndrome can be treated with medication. Some do not require treatment and will get better on their own. However, many of the underlying diseases causing nephrotic syndrome have no treatment. There remains a need for an effective treatment for nephrotic syndrome.

SUMMARY OF THE INVENTION

This invention is based on the discovery that certain yeast cells can be activated by electromagnetic fields having specific frequencies and field strengths to produce substances useful in treating nephrotic syndrome. Compositions comprising these activated yeast cells can therefore be used as a medication or dietary supplement, in the form of health drinks or dietary pills (tablets or powder). For instance, these compositions can be used to alleviate nephrotic syndrome (e.g., lower urinary protein and increase serum protein) in animals (including humans), or to prevent or postpone the onset of nephrotic syndrome in a high risk individual (e.g., someone predisposed to nephrotic syndrome because of his health or life style).

This invention embraces a composition comprising a plurality of yeast cells that have been cultured in an alternating electric field having a frequency in the range of about 9500 to 13500 MHz (e.g., 9700–10700 and 11800–12800 MHz) and a field strength in the range of about 250 to 600 mV/cm (e.g., 285–305, 285–315, 320–350, 325–355, 340–370, 360–390, 400–440, 410–450, 430–470, 440–480, 460–500 and 480–520 mV/cm). The yeast cells are cultured for a period of time sufficient to activate said plurality of yeast cells to produce substances useful in treating nephrotic syndrome in a subject. In one embodiment, the frequency and/or the field strength of the alternating electric field can be altered within the aforementioned ranges during said period of time. In other words, the yeast cells are exposed to a series of electromagnetic fields. An exemplary period of time is about 20–150 hours (e.g., 40–130 hours).

Also included in this invention is a composition comprising a plurality of yeast cells that have been cultured under acidic conditions in an alternating electric field having a frequency in the range of about 12000 to 13000 MHz (e.g., 12500–12700 MHz) and a field strength in the range of about 250 to 450 mV/cm (e.g., 360–390 or 285–315 mV/cm). In one embodiment, the yeast cells are exposed to a series of electromagnetic fields. An exemplary period of time is about 20–80 hours (e.g., 30–70 hours).

Included in this invention are also methods of making the above compositions.

Yeast cells that can be included in this composition can be derived from parent strains publically available from the China General Microbiological Culture Collection Center ("CGMCC"), China Committee for Culture Collection of Microorganisms, Institute of Microbiology, Chinese Academy of Sciences, Haidian, P.O. Box 2714, Beijing, 100080, China. Useful yeast species include, but are not limited to, those commonly used in food and pharmaceutical industries, such as *Saccharomyces cerevisiae*, *Saccharomyces carlsbergensis*, *Saccharomyces rouxii*, *Saccharomyces sake*, *Saccharomyces uvarum*, *Saccharomyces* sp., *Schizosaccharomyces pombe*, or *Rhodotorula aurantiaca*. For instance, the yeast cells can be of the strain *Saccharomyces cerevisiae* Hansen AS2.502, IFFI1010 or AS2.53, *Saccharomyces sake* Yabe ACCC2045, *Saccharomyces uvarum* Beijer IFFI1072, or *Schizosaccharomyces pombe* Lindner AS2.248. Other useful yeast strains are illustrated in Table 1.

This invention further embraces a composition comprising a plurality of yeast cells, wherein said plurality of yeast cells have been activated to treat nephrotic syndrome in a subject. Included in this invention are also methods of making these compositions.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers. A subject includes a human and veterinary subject.

Other features and advantages of the invention will be apparent from the following detailed description, and from the claims.

DETAILED DESCRIPTION OF THE INVENTION

Figure 1:
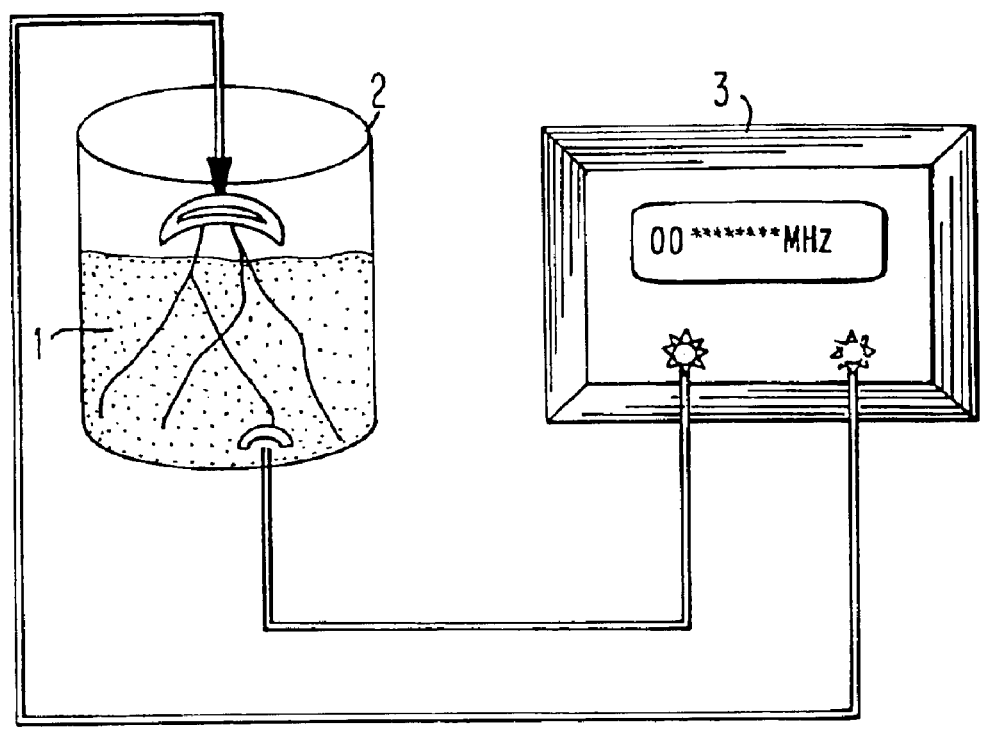
FIG. 1 is a schematic diagram showing an exemplary apparatus for activating yeast cells using electromagnetic fields. 1: yeast culture; 2: container; 3: power supply.

This invention is based on the discovery that certain yeast strains can be activated by electromagnetic fields ("EMF") having specific frequencies and field strengths to become highly efficient in producing substances that alleviate nephrotic syndrome in a subject. Compositions containing these activated yeast cells are therefore useful in the treatment of nephrotic syndrome, e.g., in decreasing urinary protein and/or increasing serum protein levels. Yeast compositions containing activated yeast cells can be used as medication, or as a dietary supplements, in the form of health drinks or dietary pills (tablets or powder).

Since the activated yeast cells contained in the yeast compositions have been cultured to endure acidic conditions (pH 2.5–4.2), these cells can survive the gastric environment and pass on to the intestines. Once in the intestines, the yeast cells are ruptured by various digestive enzymes, and the useful substances for treatment of nephrotic syndrome are released and readily absorbed.

I. Yeast Strains Useful in the Invention

The types of yeasts useful in this invention include, but are not limited to, yeasts of the genera *Saccharomyces, Schizosaccharomyces pombe* and *Rhodotorula*.

Exemplary species within the above-listed genera include, but are not limited to, those illustrated in Table 1. Yeast strains useful for this invention can be obtained from laboratory cultures, or from publically accessible culture depositories, such as CGMCC and the American Type Culture Collection, 10801 University Boulevard, Manassas, Va. 20110–2209. Non-limiting examples of useful strains (with accession numbers of CGMCC) are *Saccharomyces cerevisiae* Hansen AS2.502, IFFI1010 and AS2.53, *Saccharomyces sake* Yabe ACCC2045, *Saccharomyces uvarum* Beijer IFF11072 and *Schizosaccharomyces pombe* Lindner AS2.248. Other useful yeast strains are illustrated in Table 1.

The preparation of the yeast compositions of this invention is not limited to starting with a pure strain of yeast. A yeast composition of the invention may be produced by culturing a mixture of yeast cells of different species or strains. The ability of any activated species or strain of yeasts to treat nephrotic syndrome can be readily tested by methods known in the art. See, for instance, Examples 1 and 2.

TABLE 1

Exemplary Yeast Strains

*Saccharomyces cerevisiae* Hansen

| ACCC2034 | ACCC2035 | ACCC2036 | ACCC2037 | ACCC2038 |
|---|---|---|---|---|
| ACCC2039 | ACCC2040 | ACCC2041 | ACCC2042 | AS2.1 |
| AS2.4 | AS2.11 | AS2.14 | AS2.16 | AS2.56 |
| AS2.69 | AS2.70 | AS2.93 | AS2.98 | AS2.101 |
| AS2.109 | AS2.110 | AS2.112 | AS2.139 | AS2.173 |
| AS2.174 | AS2.182 | AS2.196 | AS2.242 | AS2.336 |
| AS2.346 | AS2.369 | AS2.374 | AS2.375 | AS2.379 |
| AS2.380 | AS2.382 | AS2.390 | AS2.393 | AS2.395 |
| AS2.396 | AS2.397 | AS2.398 | AS2.399 | AS2.400 |
| AS2.406 | AS2.408 | AS2.409 | AS2.413 | AS2.414 |
| AS2.415 | AS2.416 | AS2.422 | AS2.423 | AS2.430 |

TABLE 1-continued

Exemplary Yeast Strains

| AS2.431 | AS2.432 | AS2.451 | AS2.452 | AS2.453 |
|---|---|---|---|---|
| AS2.458 | AS2.460 | AS2.463 | AS2.467 | AS2.486 |
| AS2.501 | AS2.502 | AS2.503 | AS2.504 | AS2.516 |
| AS2.535 | AS2.536 | AS2.558 | AS2.560 | AS2.561 |
| AS2.562 | AS2.576 | AS2.593 | AS2.594 | AS2.614 |
| AS2.620 | AS2.628 | AS2.631 | AS2.666 | AS2.982 |
| AS2.1190 | AS2.1364 | AS2.1396 | IFFI1001 | IFFI1002 |
| IFFI1005 | IFFI1006 | IFFI1008 | IFFI1009 | IFFI1010 |
| IFFI1012 | IFFI1021 | IFFI1027 | IFFI1037 | IFFI1042 |
| IFFI1043 | IFFI1045 | IFFI1048 | IFFI1049 | IFFI1050 |
| IFFI1052 | IFFI1059 | IFFI1060 | IFFI1062 | IFFI1063 |
| IFFI1202 | IFFI1203 | IFFI1206 | IFFI1209 | IFFI1210 |
| IFFI1211 | IFFI1212 | IFFI1213 | IFFI1214 | IFFI1215 |
| IFFI1220 | IFFI1221 | IFFI1224 | IFFI1247 | IFFI1248 |
| IFFI1251 | IFFI1270 | IFFI1277 | IFFI1287 | IFFI1289 |
| IFFI1290 | IFFI1291 | IFFI1292 | IFFI1293 | IFFI1297 |
| IFFI1300 | IFFI1301 | IFFI1302 | IFFI1307 | IFFI1308 |
| IFFI1309 | IFFI1310 | IFFI1311 | IFFI1331 | IFFI1335 |
| IFFI1336 | IFFI1337 | IFFI1338 | IFFI1339 | IFFI1340 |
| IFFI1345 | IFFI1348 | IFFI1396 | IFFI1397 | IFFI1399 |
| IFFI1411 | IFFI1413 | IFFI1441 | IFFI1443 | |

*Saccharomyces cerevisiae* Hansen Var. *ellipsoideus* (Hansen) Dekker

| ACCC2043 | AS2.2 | AS2.3 | AS2.8 | AS2.53 |
|---|---|---|---|---|
| AS2.163 | AS2.168 | AS2.483 | AS2.541 | AS2.559 |
| AS2.606 | AS2.607 | AS2.611 | AS2.612 | |

*Saccharomyces chevalieri* Guilliermond

| AS2.131 | AS2.213 |
|---|---|

*Saccharomyces delbrueckii*

AS2.285

*Saccharomyces delbrueckii* Lindner ver. *mongolicus* (Saito) Lodder et van Rij

| AS2.209 | AS2.1157 |
|---|---|

*Saccharomyces exiguous* Hansen

| AS2.349 | AS2.1158 |
|---|---|

*Saccharomyces fermentati* (Saito) Lodder et van Rij

| AS2.286 | AS2.343 |
|---|---|

*Saccharomyces logos* van laer et Denamur ex Jorgensen

| AS2.156 | AS2.327 | AS2.335 |
|---|---|---|

*Saccharomyces mellis* (Fabian et Quinet) Lodder et kreger van Rij

AS2.195

*Saccharomyces mellis* Microellipsoides Osterwalder

AS2.699

*Saccharomyces oviformis* Osteralder

AS2.100

*Saccharomyces rosei* (Guilliermond) Lodder et Kreger van Rij

AS2.287

*Saccharomyces rouxii* Boutroux

| AS2.178 | AS2.180 | AS2.370 | AS2.371 |
|---|---|---|---|

*Saccharomyces sake* Yabe

ACCC2045

*Candida arborea*

AS2.566

*Candida lambica* (Lindner et Genoud) van. Uden et Buckley

AS2.1182

*Candida krusei* (Castellani) Berkhout

AS2.1045

TABLE 1-continued

Exemplary Yeast Strains

Candida lipolytica (Harrison) Diddens et Lodder

| | | | | |
|---|---|---|---|---|
| AS2.1207 | AS2.1216 | AS2.1220 | AS2.1379 | AS2.1398 |
| AS2.1399 | AS2.1400 | | | |

Candida parapsilosis (Ashford) Langeron et Talice Var. intermedia Van Rij et Verona

AS2.491

Candida parapsilosis (Ashford) Langeron et Talice

AS2.590

Candida pulcherrima (Lindner) Windisch

AS2.492

Candida rugousa (Anderson) Diddens et Lodder

| | | | | |
|---|---|---|---|---|
| AS2.511 | AS2.1367 | AS2.1369 | AS2.1372 | AS2.1373 |
| AS2.1377 | AS2.1378 | AS2.1384 | | |

Candida tropicalis (Castellani) Berkhout

| | | | | |
|---|---|---|---|---|
| ACCC2004 | ACCC2005 | ACCC2006 | AS2.164 | AS2.402 |
| AS2.564 | AS2.565 | AS2.567 | AS2.568 | AS2.617 |
| AS2.637 | AS2.1387 | AS2.1397 | | |

Candida utilis Henneberg Lodder et Kreger Van Rij

| | | |
|---|---|---|
| AS2.120 | AS2.281 | AS2.1180 |

Crebrothecium ashbyii (Guillermond) Routein (Eremothecium ashbyii Guilliermond)

| | | |
|---|---|---|
| AS2.481 | AS2.482 | AS2.1197 |

Geotrichum candidum Link

| | | | | |
|---|---|---|---|---|
| ACCC2016 | AS2.361 | AS2.498 | AS2.616 | AS2.1035 |
| AS2.1062 | AS2.1080 | AS2.1132 | AS2.1175 | AS2.1183 |

Hansenula anomala (Hansen)H et P sydow

| | | | | |
|---|---|---|---|---|
| ACCC2018 | AS2.294 | AS2.295 | AS2.296 | AS2.297 |
| AS2.298 | AS2.299 | AS2.300 | AS2.302 | AS2.338 |
| AS2.339 | AS2.340 | AS2.341 | AS2.470 | AS2.592 |
| AS2.641 | AS2.642 | AS2.782 | AS2.635 | AS2.794 |

Hansenula arabitolgens Fang

AS2.887

Hansenula jadinii (A. et R Sartory Weill et Meyer) Wickerham

ACCC2019

Hansenula saturnus (Klocker) H et P sydow

ACCC2020

Hansenula schneggii (Weber) Dekker

AS2.304

Hansenula subpelliculosa Bedford

| | | | | |
|---|---|---|---|---|
| AS2.740 | AS2.760 | AS2.761 | AS2.770 | AS2.783 |
| AS2.790 | AS2.798 | AS2.866 | | |

Kloeckera apiculata (Reess emend. Klocker) Janke

| | | | | |
|---|---|---|---|---|
| ACCC2022 | ACCC2023 | AS2.197 | AS2.496 | AS2.714 |
| ACCC2021 | AS2.711 | | | |

Lipomycess starkeyi Lodder et van Rij

| | |
|---|---|
| AS2.1390 | ACCC2024 |

Pichia farinosa (Lindner) Hansen

| | | | | |
|---|---|---|---|---|
| ACCC2025 | ACCC2026 | AS2.86 | AS2.87 | AS2.705 |
| AS2.803 | | | | |

Pichia membranaefaciens Hansen

| | | | |
|---|---|---|---|
| ACCC2027 | AS2.89 | AS2.661 | AS2.1039 |

Rhodosporidium toruloides Banno

ACCC2028

Rhodotorula glutinis (Fresenius) Harrison

| | | | | |
|---|---|---|---|---|
| AS2.2029 | AS2.280 | ACCC2030 | AS2.102 | AS2.107 |
| AS2.278 | AS2.499 | AS2.694 | AS2.703 | AS2.704 |
| AS2.1146 | | | | |

Rhodotorula minuta (Saito) Harrison

AS2.277

Rhodotorula rubar (Demme) Lodder

| | | | | |
|---|---|---|---|---|
| AS2.21 | AS2.22 | AS2.103 | AS2.105 | AS2.108 |
| AS2.140 | AS2.166 | AS2.167 | AS2.272 | AS2.279 |
| AS2.282 | ACCC2031 | | | |

Rhodotorula aurantiaca (Saito) Lodder

| | | | | |
|---|---|---|---|---|
| AS2.102 | AS2.107 | AS2.278 | AS2.499 | AS2.694 |
| AS2.703 | AS2.1146 | | | |

Saccharomyces carlsbergensis Hansen

| | | | | |
|---|---|---|---|---|
| AS2.113 | ACCC2032 | ACCC2033 | AS2.312 | AS2.116 |
| AS2.118 | AS2.121 | AS2.132 | AS2.162 | AS2.189 |
| AS2.200 | AS2.216 | AS2.265 | AS2.377 | AS2.417 |
| AS2.420 | AS2.440 | AS2.441 | AS2.443 | AS2.444 |
| AS2.459 | AS2.595 | AS2.605 | AS2.638 | AS2.742 |
| AS2.745 | AS2.748 | AS2.1042 | | |

Saccharomyces uvarum Beijer

| | | | | |
|---|---|---|---|---|
| IFFI1023 | IFFI1032 | IFFI1036 | IFFI1044 | IFFI1072 |
| IFFI1205 | IFFI1207 | | | |

Saccharomyces willianus Saccardo

| | | | | |
|---|---|---|---|---|
| AS2.5 | AS2.7 | AS2.119 | AS2.152 | AS2.293 |
| AS2.381 | AS2.392 | AS2.434 | AS2.614 | AS2.1189 |

Saccharomyces sp.

AS2.311

Saccharomycodes ludwigii Hansen

| | | |
|---|---|---|
| ACCC2044 | AS2.243 | AS2.508 |

Saccharomycodes sinenses Yue

AS2.1395

Schizosaccharomyces octosporus Beijerinck

| | |
|---|---|
| ACCC2046 | AS2.1148 |

Schizosaccharomyces pombe Lindner

| | | | | |
|---|---|---|---|---|
| ACCC2047 | ACCC2048 | AS2.214 | AS2.248 | AS2.249 |
| AS2.255 | AS2.257 | AS2.259 | AS2.260 | AS2.274 |
| AS2.994 | AS2.1043 | AS2.1149 | AS2.1178 | IFFI1056 |

Sporobolomyces roseus Kluyver et van Niel

| | | | | |
|---|---|---|---|---|
| ACCC2049 | ACCC2050 | AS2.19 | AS2.962 | AS2.1036 |
| ACCC2051 | AS2.261 | AS2.262 | | |

Torulopsis candida (Saito) Lodder

| | |
|---|---|
| AS2.270 | ACCC2052 |

Torulopsis famta (Harrison) Lodder et van Rij

| | |
|---|---|
| ACCC2053 | AS2.685 |

Torulopsis globosa (Olson et Hammer) Lodder et van Rij

| | |
|---|---|
| ACCC2054 | AS2.202 |

Torulopsis inconspicua Lodder et Kreger van Rij

AS2.75

Trichosporon behrendii Lodder et Kreger van Rij

| | |
|---|---|
| ACCC2056 | AS2.1193 |

Trichosporon capitatum Diddens et Lodder

| | |
|---|---|
| ACCC2056 | AS2.1385 |

TABLE 1-continued

Exemplary Yeast Strains

*Trichosporon cutaneum* (de Beurm et al.) Ota

| ACCC2057 | AS2.25 | AS2.570 | AS2.571 | AS2.1374 |
|---|---|---|---|---|
| | *Wickerhamia fluorescens* (Soneda) Soneda | | | |
| ACCC2058 | AS2.1388 | | | |

II. Application of Electromagnetic Fields

An electromagnetic field useful in this invention can be generated and applied by various means well known in the art. For instance, the EMF can be generated by applying an alternating electric field or an oscillating magnetic field.

Alternating electric fields can be applied to cell cultures through electrodes in direct contact with the culture medium, or through electromagnetic induction. See, e.g., FIG. 1. Relatively high electric fields in the medium can be generated using a method in which the electrodes are in contact with the medium. Care must be taken to prevent electrolysis at the electrodes from introducing undesired ions into the culture and to prevent contact resistance, bubbles, or other features of electrolysis from dropping the field level below that intended. Electrodes should be matched to their environment, for example, using Ag—AgCl electrodes in solutions rich in chloride ions, and run at as low a voltage as possible. For general review, see Goodman et al., *Effects of EMF on Molecules and Cells*, International Review of Cytology, A Survey of Cell Biology, Vol. 158, Academic Press, 1995.

The EMFs useful in this invention can also be generated by applying an oscillating magnetic field. An oscillating magnetic field can be generated by oscillating electric currents going through Helmholtz coils. Such a magnetic field in turn induces an electric field.

The frequencies of EMFs useful in this invention range from about 9500 to 13500 MHz (e.g., 9700–10700 and 11800–12800 MHz). Exemplary frequencies are 10156, 10185, 12107, 12687 and 12698 MHz. The field strength of the electric field useful in this invention ranges from about 250 to 600 mV/cm (e.g., 285–305, 285–315, 320–350, 325–355, 340–370, 360–390, 400–440, 410–450, 430–470, 440–480, 460–500 and 480–520 mV/cm). Exemplary field strengths are 296, 332, 353, 364, 373, 416, 435, 443, 456, 487 and 507 mV/cm.

When a series of EMFs are applied to a yeast culture, the yeast culture can remain in the same container while the same set of EMF generator and emitters is used to change the frequency and/or field strength. The EMFs in the series can each have a different frequency or a different field strength; or a different frequency and a different field strength. Such frequencies and field strengths are preferably within the above-described ranges. Although any practical number of EMFs can be used in a series, it may be preferred that the yeast culture be exposed to, for example, a total of 2, 3, 4, 5, 6, 7, 8, 9, 10, 11, 12, 13 or more EMFs in a series. In one embodiment, the yeast culture is exposed to a series of EMFs, wherein the frequency of the electric field is alternated in the range of 9700–10700 and 11800–12800 MHz.

Although the yeast cells can be activated after even a few hours of culturing in the presence of an EMF, it may be preferred that the activated yeast cells be allowed to multiply and grow in the presence of the EMF(s) for a total of 20–150 hours (e.g., 40–120 hours).

FIG. 1 illustrates an exemplary apparatus for generating alternating electric fields. An electric field of a desired frequency and intensity is generated by an AC source (3) capable of generating an alternating electric field, preferably in a sinusoidal wave form, in the frequency range of 10 to 20,000 MHz. Signal generators capable of generating signals with a narrower frequency range can also be used. If desirable, a signal amplifier can also be used to increase the output. The activation container (2) can be made from non-conductive material, e.g., plastics, glass or ceramic. The wire connecting the activation container (2) and the signal generator (3) is preferably a high frequency coaxial cable with a transmission frequency of at least 30 GHz.

The alternating electric field can be applied to the culture by a variety of means, including placing the yeast culture (1) in close proximity to the signal emitters such as a metal wire or tube capable of transmitting EMFs. The metal wire or tube can be made of red copper, and be placed inside the container (2), reaching as deep as 3–30 cm. For example, if the fluid in the container (2) has a depth of 15–20 cm, 20–30 cm, 30–50 cm, 50–70 cm, 70–100 cm, 100–150 cm or 150–200 cm, the metal wire can be 3–5 cm, 5–7 cm, 7–10 cm, 10–15 cm, 15–20 cm, 20–30 cm and 25–30 cm from the bottom of the container (2), respectively. The number of electrode wires used depends on the volume of the culture as well as the diameter of the wires. The number of metal wires/tubes used can be from 1 to 10 (e.g., 2 to 3). It is recommended, though not mandated, that for a culture having a volume up to 10 L, metal wires/tubes having a diameter of 0.5 to 2.0 mm be used. For a culture having a volume between 10 L and 100 L, metal wires/tubes having a diameter of 3.0 to 5.0 mm can be used. For a culture having a volume in the range of 100–1000 L, metal wires/tubes having a diameter of 6.0 to 15.0 mm can be used. For a culture having a volume greater than 1000 L, metal wires/tubes having a diameter of 20.0 to 25.0 mm can be used.

In one embodiment, the electric field is applied by electrodes submerged in the culture (1). In this embodiment, one of the electrodes can be a metal plate placed on the bottom of the container (2), and the other electrode can comprise a plurality of electrode wires evenly distributed in the culture (1) so as to achieve even distribution of the electric field energy. The number of electrode wires used depends on the volume of the culture as well as the diameter of the wires.

III. Culture Media

Culture media useful in this invention contain sources of nutrients assimilable by yeast cells. Complex carbon-containing substances in a suitable form, such as carbohydrates (e.g., sucrose, glucose, fructose, dextrose, maltose, xylose, cellulose, starches, etc.) and coal, can be the carbon sources for yeast cells. The exact quantity of the carbon sources utilized in the medium can be adjusted in accordance with the other ingredients of the medium. In general, the amount of carbohydrates varies between about 0.1% and 10% by weight of the medium and preferably between about 0.1% and 5% (e.g., about 2%). These carbon sources can be used individually or in combination. Amino acid-containing substances in suitable form (e.g., beef extract and peptone) can also be added individually or in combination. In general, the amount of amino acid containing substances varies between about 0.1% and 0.5% by weight of the medium and preferably between about 0.1% and 0.3% (e.g., about 0.25%). Among the inorganic salts which can be added to the culture medium are the customary salts capable of yielding sodium, potassium, calcium, phosphate, sulfate, carbonate, and like ions. Non-limiting examples of nutrient inorganic salts are $(NH_4)_2HPO_4$, $KH_2PO_4$, $K_2HPO_4$, $CaCO_3$, $MgSO_4$, $NaCl$, and $CaSO_4$.

IV. Electromagnetic Activation of Yeast Cells

To activate or enhance the ability of yeast cells to produce substances beneficial for the treatment of nephrotic syndrome (e.g., decreasing urinary protein and/or increasing serum protein levels), these cells can be activated by being cultured in an appropriate medium under sterile conditions at 20° C.–38° C., preferably at 28–32° C. (e.g., 30° C.) for a sufficient amount of time, e.g., 5–200 hours (e.g., 6–16, 10–20, 27–37 and 31–41 hours), in an alternating electric field or a series of alternating electric fields as described above.

An exemplary culture medium is made by mixing 1000 ml of distilled water with 18 g of mannitol, 40 µg of vitamin $B_{12}$, 30 µg of vitamin E, 30 µg of vitamin H, 35 ml of fetal bovine serum, 0.20 g of $KH_2PO_4$, 0.25 g of $MgSO_4 * 7H_2O$, 0.3 g of NaCl, 0.2 g of $CaSO_4 * 2H_2O$, 4.0 g of $CaCO_3 * 5H_2O$, and 2.5 g of peptone.

An exemplary set-up of the culturing process is depicted in FIG. 1. Untreated yeast cells are added to a culture medium at $1 \times 10^8$ cells per 1000 ml of the culture medium. The yeast cells may be *Saccharomyces cerevisiae* Hansen AS2.502, or may be selected from any of the strains listed in Table 1. An exemplary activation process of the yeast cells involves the following sequence: the yeast cells are grown in the culture medium for 23–33 hours (e.g., 28 hours) at 28–32° C. and then exposed to (1) an alternating electric field having a frequency of 10156 MHz and a field strength in the range of 325–355 mV/cm (e.g., 332 mV/cm) for 6–16 hours (e.g., 11 hours); (2) then to an alternating electric field having a frequency of 10185 MHz and a field strength in the range of 400–440 mV/cm (e.g., 416 mV/cm) for 31–41 hours (e.g., 36 hours); (3) then to an alternating electric field having a frequency of 12107 MHz and a field strength in the range of 430–470 mV/cm (e.g., 443 mV/cm) for 27–37 hours (e.g., 32 hours); (4) then to an alternating electric field having a frequency of 12687 MHz and a field strength in the range of 340–370 mV/cm (e.g., 353 mV/cm) for 31–41 hours (e.g., 36 hours); and (5) finally to an alternating electric field having a frequency of 12698 MHz and a field strength in the range of 285–305 mV/cm (e.g., 296 mV/cm) for 10–20 hours (e.g., 15 hours). The activated yeast cells are then recovered from the culture medium by various methods known in the art, dried (e.g., by lyophilization) and stored at about 4° C. in powder form. The resultant yeast powder preferably contains no less than $10^{10}$ cells/g activated yeast.

Subsequently, the activated yeast cells can be evaluated for their ability to treat nephrotic syndrome using standard methods known in the art, such as those described in Section VII.

V. Acclimatization of Yeast Cells To the Gastric Environment

Because the activated yeast cells of this invention must pass through the stomach before reaching the small intestine, where the effective components are released from these yeast cells, it is preferred that these yeasts be cultured under acidic conditions so as to acclimatize the cells to the gastric juice. This acclimatization process results in better viability of the yeast cells in the acidic gastric environment.

To achieve this, the yeast powder containing activated yeast cells can be mixed with a highly acidic acclimatizing culture medium at 10 g (containing more than $10^{10}$ activated cells per gram) per 1000 ml. The yeast mixture can then be cultured first in the presence of an alternating electric field having a frequency of 12687 MHz and a field strength in the range of 360–390 mV/cm (e.g., 364 mV/cm) at about 28 to 32° C. for 36–48 hours (e.g., 44 hours). The resultant yeast cells can then be further incubated in the presence of an alternating electric field having a frequency of 12698 MHz and a field strength in the range of 285–315 mV/cm (e.g., 296 mV/cm) at about 28 to 32° C. for 16–28 hours (e.g., 20 hours). The resulting acclimatized yeast cells are then recovered from the culture medium by various methods known in the art and are dried and stored either in powder form ($\geq 10^{10}$ cells/g) at room temperature or in vacuum at 0–4° C.

An exemplary acclimatizing culture medium is made by mixing 700 ml fresh pig gastric juice and 300 ml wild Chinese hawthorn extract. The pH of acclimatizing culture medium is adjusted to 2.5 with 0.1 M hydrochloric acid (HCl) and 0.2 M potassium hydrogen phthalate ($C_6H_4$(COOK)COOH). The fresh pig gastric juice is prepared as follows. At about 4 months of age, newborn Holland white pigs are sacrificed, and the entire contents of their stomachs are retrieved and mixed with 2000 ml of water under sterile conditions. The mixture is then allowed to stand for 6 hours at 4° C. under sterile conditions to precipitate food debris. The supernatant is collected for use in the acclimatizing culture medium. To prepare the wild Chinese hawthorn extract, 500 g of fresh wild Chinese hawthorn is dried under sterile conditions to reduce water content ($\leq 8\%$). The dried fruit is then ground ($\geq 20$ mesh) and added to 1500 ml of sterilized water. The hawthorn slurry is allowed to stand for 6 hours at 4° C. under sterile conditions. The hawthorn supernatant is collected to be used in the acclimatizing culture medium.

VI. Manufacture of Yeast Compositions

Figure 2:
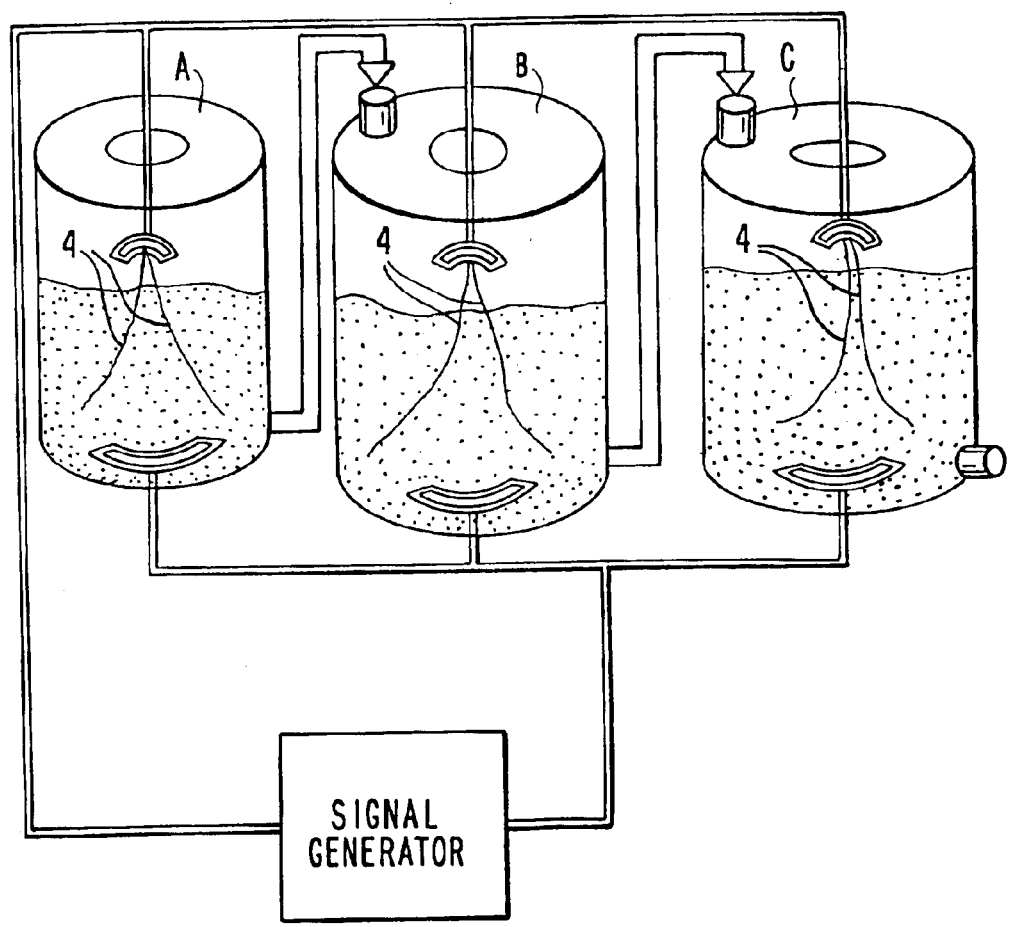
FIG. 2 is a schematic diagram showing an exemplary apparatus for making yeast compositions of the invention. The apparatus comprises a signal generator and interconnected containers A, B and C.

To prepare the yeast compositions of the invention, an apparatus depicted in FIG. 2 or an equivalent thereof can be used. This apparatus includes three containers, a first container (A), a second container (B), and a third container (C), each equipped with a pair of electrodes (4). One of the electrodes is a metal plate placed on the bottom of the containers, and the other electrode comprises a plurality of electrode wires evenly distributed in the space within the container to achieve even distribution of the electric field energy. All three pairs of electrodes are connected to a common signal generator.

The culture medium used for this purpose is a mixed fruit extract solution containing the following ingredients per 1000 L: 300 L of wild Chinese hawthorn extract, 300 L of jujube extract, 300 L of *Schisandra chinensis* (*Turez*) *Baill* seeds extract, and 100 L of soy bean extract. To prepare hawthorn, jujube and *Schisandra chinensis* (*Turez*) *Baill* seeds extracts, the fresh fruits are washed and dried under sterile conditions to reduce the water content to no higher than 8%. One hundred kilograms of the dried fruits are then ground ($\geq 20$ mesh) and added to 400 L of sterilized water. The mixtures are stirred under sterile conditions at room temperature for twelve hours, and then centrifuged at 1000 rpm to remove insoluble residues. To make the soy bean extract, fresh soy beans are washed and dried under sterile conditions to reduce the water content to no higher than 8%. Thirty kilograms of dried soy beans are then ground into particles of no smaller than 20 mesh, and added to 130 L of sterilized water. The mixture is stirred under sterile conditions at room temperature for twelve hours and centrifuged at 1000 rpm to remove insoluble residues. Once the mixed fruit extract solution is prepared, it is autoclaved at 121° C. for 30 minutes and cooled to below 40° C. before use.

One thousand grams of the activated yeast powder prepared as described above (Section V, supra) is added to 1000 L of the mixed fruit extract solution, and the yeast solution is transferred to the first container (A) shown in FIG. 2. The yeast cells are then cultured in the presence of an alternating electric field having a frequency of 12687 MHz and a field strength of about 460–500 mV/cm (e.g., 487 mV/cm) at 28–32° C. under sterile conditions for 27–37 hours (e.g., 32 hours). The yeast cells are further incubated in an alternating electric field having a frequency of 12698 MHz and a field strength of 410–450 mV/cm (e.g., 435 mV/cm). The culturing continues for 7–17 hours (e.g., 12 hours).

The yeast culture is then transferred from the first container (A) to the second container (B) (if need be, a new batch of yeast culture can be started in the now available the first container (A)), and subjected to an alternating electric field having a frequency of 12687 MHz and a field strength of 480–520 mV/cm (e.g., 507 mV/cm) for 19–29 hours (e.g., 24 hours). Subsequently the frequency and field strength of the electric field are changed to 12698 MHz and 440–480 mV/cm (e.g., 456 mV/cm), respectively. The culturing process continues for 7–17 hours (e.g., 12 hours).

The yeast culture is then transferred from the second container (B) to the third container (C), and subjected to an alternating electric field having a frequency of 12687 MHz and a field strength of 360–390 mV/cm (e.g., 373 mV/cm) for 19–29 hours (e.g., 24 hours). Subsequently the frequency and field strength of the electric field are changed to 12698 MHz and 320–350 mV/cm (e.g., 332 mV/cm), respectively. The culturing continues for 7–17 hours (e.g., 12 hours).

The yeast culture from the third container (C) can then be packaged into vacuum sealed bottles, each having 30–50 ml or 100 ml of the yeast culture, for use as a dietary supplement, e.g., health drinks, or medication in the form of pills, powder, etc. If desired, the final yeast culture can also be dried within 24 hours and stored in powder form. The dietary supplement can be taken orally three times daily at 30 ml per dose for a three-month period, preferably before meals.

In some embodiments, the compositions of the invention can also be administered intravenously or peritoneally in the form of a sterile injectable preparation. Such a sterile preparation can be prepared as follows. A sterilized health drink composition is first treated under ultrasound ($\geq 18000$ Hz) for 10 minutes and then centrifuged at 4355 rpm for another 10 minutes. The resulting supernatant is adjusted to pH 7.2–7.4 using 1 M NaOH and subsequently filtered through a membrane (0.22 $\mu$m for intravenous injection and 0.45 $\mu$m for peritoneal injection) under sterile conditions. The resulting sterile preparation is submerged in a 35–38° C. water bath for 30 minutes before use. In other embodiments, the compositions of the invention may also be formulated with pharmaceutically acceptable carriers to be orally administered in any orally acceptable dosage form including, but not limited to, capsules, tablets, suspensions or solutions.

The yeast compositions of the present invention are derived from yeasts used in food and pharmaceutical industries. The yeast compositions are thus devoid of side effects associated with many pharmaceutical compounds.

VII. Examples

In order that this invention be more fully understood, the following examples are set forth. These examples are for the purpose of illustration only and are not to be construed as limiting the scope of the invention in any way.

The activated yeast compositions used in the following examples were prepared as described above, using *Saccharomyces cerevisiae* Hansen AS2.502, cultured in the presence of an alternating electric field having the electric field frequency and field strength exemplified in the parentheses following the recommended ranges listed in Section IV, supra. Control (i.e., untreated) yeast compositions were those prepared in the same manner as described in Section VI, supra, except that the yeast cells were cultured in the absence of EMFs. Unless otherwise specified, all compositions of interest were administered to the animals by intragastric feeding.

Example 1

Effect of Treatment on Proteinuria

To test the ability of the activated yeast compositions to reduce the level of urinary protein, sixty healthy Wistar rats with average weight of about 200–220 g (4–7 months old, half of them male and the other half female) were chosen and males and females were kept in separate cages. Each rat was injected intravenously with bovine serum albumin (BSA; at 350 mg/kg body weight) in the marginal ear vein to induce excess secretion of protein in the urine (proteinuria). After the injection, each rat was given normal feed for seven days. Urine samples were collected from the fine cancellated base of metabolic cages, and the amount of protein in the samples was determined by hot acetic acid method. Forty rats were selected for further study from those showing proteinuria, i.e., less than 0.5 mg/24 hours, and randomly divided into four equal groups, designated as AY, NY, CK1 and CK2.

Subsequently, a composition of interest was administered twice daily to each of the four groups of rats for eight weeks. Rats in the AY, NY and CK1 groups received the 1.0 ml/100 g body weight of the activated yeast composition, the control yeast composition and saline, respectively. Rats in the CK2 group received 0.25 mg/100 g body weight of pednisone (metacortandiacin). Urine samples were collected for 24 hours on the last day of the fourth week as well as on the last day of the eighth week.

The amount of urinary protein was determined by sulfosalicylic acid turbidimetry. The volume of each urine sample was first measured (ml). Five milliliters of each sample was then taken out and centrifuged at 3000 rpm. One milliliter of the supernatant was mixed with 3 ml of 30 mg/ml sulfosalicylic acid in a test tube. In the control tube, 1 ml saline was mixed with 3 ml of 30 mg/ml sulfosalicylic acid. Ten minutes later, the absorption of the sample test tube was measured at 620 nm against the control tube. The amount of urinary protein (per 100 ml) was determined based on a protein standard curve.

The protein standard curve was created according to the following procedure. The amount of protein in fresh sera free of unhemolysis and unbilirubin were determined by commonly used Kjeldahl's method. The fresh sera were then diluted to 4 mg/ml with saline. Seven mixtures were prepared according to Table 2. Absorption was determined for each mixture containing diluted sera against the control mixture, which had no serum. The protein standard curve was thus created with protein concentrations and their corresponding absorption.

TABLE 2

| Tube # | 1 | 2 | 3 | 4 | 5 | 6 | Control |
|---|---|---|---|---|---|---|---|
| 4 mg/ml Serum (ml) | 0.0125 | 0.025 | 0.05 | 0.1 | 0.2 | 0.4 | 0 |
| Saline (ml) | 0.9875 | 0.975 | 0.95 | 0.9 | 0.8 | 0.6 | 1.0 |
| 30 mg/ml | 3.0 | 3.0 | 3.0 | 3.0 | 3.0 | 3.0 | 3.0 |

TABLE 2-continued

| Tube # | 1 | 2 | 3 | 4 | 5 | 6 | Control |
|---|---|---|---|---|---|---|---|
| Sulfosalicylic acid (ml) | | | | | | | |
| Protein Conc. (mg %) | 5.0 | 10.0 | 20.0 | 40.0 | 80.0 | 160.0 | 0.0 |

The amount urinary protein (mg) in 100 ml urine samples was calculated by multiplying urinary protein concentration (mg %) by the total urine volume in the 24-hour collection period (ml) and divided by 100 and summarized in Table 3.

TABLE 3

The Effect of Treatment on Urinary Protein secretion

| | Urinary Protein (mg in 100 ml urine sample) in a 24-hour Period | |
|---|---|---|
| Group | 4-Week Treatment | 8-Week Treatment |
| CK1 | 7.21 ± 2.34 | 7.43 ± 2.52 |
| CK2 | 4.57 ± 1.42 | 4.22 ± 1.34 |
| NY | 7.33 ± 2.45 | 7.41 ± 2.42 |
| AY | 0.62 ± 0.21 | 0.34 ± 0.14 |

The results in Table 3 show that the activated yeast composition was more effective in reducing the amount of urinary protein than the control yeast composition, saline or pednisone.

Example 2

Effect of Treatment on Serum Protein

To test the ability of the activated yeast compositions to reduce the level of urinary protein, sixty healthy Wistar rats with average weight of about 200-220 g (4–6 months old, half of them male and the other half female) were chosen and prepared as described in Example 1.

Subsequently, a composition of interest was administered twice daily to each of the four groups of rats for six weeks. Rats in the AY, NY and CK1 groups received 1.0 ml/100 g body weight of the activated yeast composition, the control yeast composition and saline, respectively. Rats in the CK2 group received 0.2 mg/100 g body weight of pednisone. Six weeks later, the rats were anesthetized with ether and blood samples were collected from the carotid artery and centrifuged at 3000 rpm. The amount of protein in the supernatant (serum protein) was determined.

To determine the amount of serum protein, 50 μl of the supernatant and standard serum protein were added into two separate tubes. Four milliliters of allophanamide (biuret) was added to each tube and mixed with the samples. The mixtures were placed in water bath at 37° C. for 10 minutes and measured for absorption at 546 nm. The concentration of serum protein was calculated according to the following formula:

[Serum Protein]=[absorption for the testing sample/absorption for the standard]×[standard serum protein]($g/dl$).

The results are summarized in Table 4.

TABLE 4

The Effect of Treatment on Serum Protein

| Group | Treatment | Serum Protein (g/dl) |
|---|---|---|
| CK1 | Saline (1.0 ml/100 g) | 4.72 ± 2.33 |
| CK2 | Pednisone (0.2 mg/100 g) | 6.41 ± 3.32 |
| NY | Control Yeast Composition (1.0 ml/100 g) | 4.64 ± 2.44 |
| AY | Activated Yeast Composition (1.0 ml/100 g) | 8.86 ± 3.26 |

The results in Table 4 show that unlike the control yeast composition, saline or pednisone, the activated yeast composition was effective in increasing serum protein level in subjects with hypoalbuminemia.

While a number of embodiments of this invention have been set forth, it is apparent that the basic constructions may be altered to provide other embodiments which utilize the compositions and methods of this invention.

What is claimed:

1. A composition comprising a plurality of yeast cells, wherein said plurality of yeast cells are characterized by their ability to treat nephrotic syndrome in a subject, said ability resulting from their having been cultured in the presence of an alternating electric field having a frequency in the range of 9500 to 13500 MHz and a field strength in the range of 250 to 600 mV/cm, as compared to yeast cells not having been so cultured.

2. The composition of claim 1, wherein said frequency is in the range of 9700–10700 or 11800–12800 MHz.

3. The composition of claim 1, wherein said field strength is in the range of 285–305, 285–315, 320–350, 325–355, 340–370, 360–390, 400–440, 410–450, 430–470, 440–480, 460–500 or 480–520 mV/cm.

4. The composition of claim 1, wherein said yeast cells are cells of the species *Saccharomyces cerevisiae, Saccharomyces carlsbergensis, Saccharomyces rouxii, Saccharomyces sake, Saccharomyces uvarum, Saccharomyces sp., Schizosaccharomyces pombe*, or *Rhodotorula aurantiaca*.

5. The composition of claim 1, wherein said yeast cells are cells of the strain deposited at the China General Microbiological Culture Collection Center with an accession number selected from the group consisting of AS2.502, IFFI1010, AS2.53, ACCC2045, IFFI1072 and AS2.248.

6. The composition of claim 1, wherein said composition is in the form of a tablet, powder, or a health drink.

7. The composition of claim 6, wherein said composition is in the form of a health drink.

8. The composition of claim 1, wherein said nephrotic syndrome is caused by minimal change disease, focal segmental glomerular sclerosis, membranous glomerulonephritis or mesangial proliferative glomerulonephritis.

9. A method of preparing a yeast composition, comprising culturing a plurality of yeast cells in the presence of an alternating electric field having a frequency in the range of 9500 to 13500 MHz and a field strength in the range of 250 to 600 mV/cm for a period of time, wherein said composition is capable of treating nephrotic syndrome in a subject as compared to yeast cells not having been so cultured.

10. The method of claim 9, wherein said frequency is in the range of 9700–10700 or 11800–12800 MHz.

11. A method for treating nephrotic syndrome in a subject, comprising administering to said subject the composition of claim 1.

12. The method of claim 11 comprising oral administration.

* * * * *

UNITED STATES PATENT AND TRADEMARK OFFICE
CERTIFICATE OF CORRECTION

PATENT NO. : 6,977,168 B2 Page 1 of 1
APPLICATION NO. : 10/717133
DATED : December 20, 2005
INVENTOR(S) : Ling Yuk Cheung It is certified that error appears in the above-identified patent and that said Letters Patent is hereby corrected as shown below:

Column 3, line 41:  "IFF11072" should read --IFFI1072--.

Column 9, line 15:  "$MgSO_4*7H_2O$" should read --$MgSO_4 \cdot 7H_2O$--

Column 9, line 16:  "$CaSO_{4*}2H_2O$" should read --$CaSO_4 \cdot 2H_2O$--

Column 9, line 16:  "$CaCO_{3*}5H_2O$" should read --$CaCO_3 \cdot 5H_2O$--

Signed and Sealed this

Nineteenth Day of December, 2006

JON W. DUDAS
*Director of the United States Patent and Trademark Office*